US008621911B2

(12) United States Patent
McFaul (10) Patent No.: US 8,621,911 B2
(45) Date of Patent: Jan. 7, 2014

(54) METHOD AND SYSTEM FOR DETERMINING LEVELS OF GASES

(76) Inventor: William J. McFaul, Jackson, NJ (US)

( * ) Notice: Subject to any disclaimer, the term of this patent is extended or adjusted under 35 U.S.C. 154(b) by 329 days.

(21) Appl. No.: 13/013,374

(22) Filed: Jan. 25, 2011

(65) Prior Publication Data

US 2011/0277536 A1  Nov. 17, 2011

Related U.S. Application Data

(60) Provisional application No. 61/334,642, filed on May 14, 2010.

(51) Int. Cl.
*G01N 33/18* (2006.01)

(52) U.S. Cl.
USPC ............................. 73/19.1; 436/116; 436/121

(58) Field of Classification Search
USPC ................................... 73/19.1; 436/116, 121
See application file for complete search history.

(56) References Cited

U.S. PATENT DOCUMENTS

| 3,909,204 | A | * | 9/1975 | Allen ........................... 422/90 |
| 4,288,062 | A | * | 9/1981 | Gupta et al. ................. 266/88 |
| 4,319,479 | A | * | 3/1982 | Iwamura et al. ............ 73/19.02 |
| 5,006,311 | A | * | 4/1991 | Hoots et al. ................. 422/62 |
| 5,101,671 | A | * | 4/1992 | Elgas .......................... 73/863.23 |
| 5,154,809 | A | * | 10/1992 | Oren et al. .................. 204/524 |
| 5,292,666 | A | * | 3/1994 | Fabinski et al. ............. 436/114 |
| 5,726,565 | A | * | 3/1998 | Uchiyama et al. .......... 324/94 |
| 5,885,842 | A | * | 3/1999 | Lai .............................. 436/116 |
| 5,922,610 | A |   | 7/1999 | Alving et al. |
| 5,932,791 | A | * | 8/1999 | Hambitzer et al. .......... 73/19.01 |
| 6,277,329 | B1 | * | 8/2001 | Evans ........................... 422/80 |
| 6,968,679 | B2 | * | 11/2005 | Pott .............................. 60/285 |
| 7,101,340 | B1 |   | 9/2006 | Braun |
| 2002/0193698 | A1 |   | 12/2002 | Moilanen et al. |
| 2005/0053549 | A1 |   | 3/2005 | Parikh et al. |
| 2008/0077037 | A1 |   | 3/2008 | Gouma et al. |

OTHER PUBLICATIONS

Supkis, Daniel E., "A greenhouse gas is used in the treatment of respiratory failure," ASTM Standardization News, Sep. 2000. pp. 1-3. Accessed online on Feb. 16, 2013 at <www.astm.org>.*
"Nitric Oxide Therapy," Critial Care Therapy and Respiratory Care Section. National Institutes of Health. May 2000. Accessed online on Feb. 16, 2013 at <http://clinicalcenter.nih.gov>.*
"Occupational Health Guideline for Nitric Oxide." U. S. Department of Health and Human Services. pp. 1-4. Sep. 1978.*
S.C. Body, P.M. Hartigan, S.K. Shernan, V. Formanek, W.E. Hurford, "Nitric Oxide: Delivery, Measurement, and Clinical Application," Journal of Cardiothoracis and Vascualr Anesthesia, vol. 9, No. 6, pp. 748-763. Dec. 1995.*
"Carbon Monoxide," 29 CFR 1917.24, Occupational Safety & Health Administration. Jul. 1997.*
Weinberger B., Laskin D. L., Heck D. E., Laskin J. D., "The toxicology of inhaled nitric oxide," Toxicol. Sci. (2001) 59 (1): 5-16.*
International Search Report dated Dec. 26, 2011. KR is the International Searching Authority.

* cited by examiner

*Primary Examiner* — Lisa Caputo
*Assistant Examiner* — Punam Roy
(74) *Attorney, Agent, or Firm* — Licata & Tyrrell P.C.

(57) ABSTRACT

A method and system for measuring or assessing the homeostatic relationship between gases in the body, environment or water. The measured or assessed level of gases in the body, environment or air uses the interrelationships of the various components in order to establish guidelines for treating individuals, the environment or water.

6 Claims, 12 Drawing Sheets

METHOD AND SYSTEM FOR DETERMINING LEVELS OF GASES

This application claims the benefit of U.S. Provisional Application Ser. No. 61/334,642, filed May 14, 2010, the contents of which are incorporated herein by reference.

BACKGROUND OF THE INVENTION

1. Field of the Invention

The present invention relates to the field of measuring the levels of gases in the body of individuals or the environment for treatment.

2. Description of the Related Technology

All forms of life are supported by a variety of substances; including but not limited to hormones, proteins, peptides, amino acids, minerals (ions), vitamins (chemicals or compounds that function as vitamins) and bacteria. These substances create the homeostasis essential to maintain life for humans as well as plants and animals.

Current scientific findings have not identified that some pairs of substances affect levels of each other in the body. Furthermore, certain other substances modulate (regulate) levels of the pairs of substances. Additionally, certain substances are a part of more than one modulated pair of substances. These relationships can be utilized in order to determine various health parameters of an individual, however, to date; these corollary relationships have not been established in order to effectively use them.

Therefore, there is a need in the field to identify and utilize the homeostatic relationship between the substances that are important to the body's functioning via the measuring of various levels of the substances that are part of these pairings. There is also a need to utilize the homeostatic relationships in order to analyze different environments.

SUMMARY OF THE INVENTION

An object of the invention is the establishing of a treatment based upon gases in the body.

Another object of the invention is remediation of imbalances in relationships between gases in the body.

Still yet another object of the invention of the invention is the establishing of a treatment based upon gases in an environment.

Another object of the invention is remediation of imbalances in relationships between gases in an environment.

Still yet another object of the invention of the invention is the establishing of a treatment based upon gases in water.

Another object of the invention is remediation of imbalances in relationships between gases in water.

An aspect of the present invention may be a method for treating an individual by comparing levels of gases in an individual: measuring a level of nitric oxide in the individual; measuring a level of carbon monoxide in the individual; measuring a level of hydrogen sulfide in the individual; comparing the measured levels; and establishing a treatment based upon the compared measured levels.

Another aspect of the present invention may be a method for establishing a treatment by comparing levels of gases in an environment: measuring a level of nitric oxide in the environment; measuring a level of carbon monoxide in the environment; measuring a level of hydrogen sulfide in the environment; comparing the measured levels; and establishing a treatment based upon the compared measured levels.

Still yet another aspect of the present invention may be a method for establishing a treatment by comparing levels of gases in water; measuring a level of nitric oxide in the water; measuring a level of carbon monoxide in the water; measuring a level of hydrogen sulfide in the water; comparing the measured levels; and establishing a diagnosis based upon the compared measured levels.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

All forms of life are supported by modulated pairs of substances. These substances create the homeostasis essential to maintain life for humans as well as animals.

Several terms are used herein and are defined as follows:

The term "modulator" means an agent, substance or mechanism that facilitates the maintenance of homeostasis between pairs. "Pairs" may be hormones, minerals, proteins, amino acids, bacteria, virus, gases and natural processes. The agent can decrease intensity of stimulatory processes or substances, or increase intensity of compensatory ones.

The term "catalyst" means the driver which initiates modulation to take place. Such catalysts can include enzymes, hormones, RNA, gases and countless signaling mechanisms.

The term "gas" refers to all compounds and molecules that are distinguished from the solid and liquid states by relatively low density and viscosity and relatively great expansion.

The term "Homeostatic Relationship (Homeostasis)" means the balance or equilibrium between two substances.

The relationship does not have to be 50%-50% but can vary depending upon the two substances in question.

The term "Extracellular Matter (ECM)" means all body fluid outside of cells and blood; including but not limited to cerebrospinal fluid, lymph, chyle, interstitial fluid, saliva, transcellular fluid, amniotic fluid, sperm, and sputum.

The term "Mental Functioning Activity (MFA)" means the rate of activity attributable to the neural firing rate in the brain and elsewhere in the body.

The invention addresses the diagnostic analysis of the corollary relationships between gases that provide and maintain homeostasis in an individual as well as within the environment.

The data for measuring homeostasis between gases within a modulated pair can vary from one individual or specimen to another due to environmental factors, basic metabolism, genetic make-up and other factors. Accordingly, a range of homeostatic relationships will need to be determined for all modulated pairs in order to assess deviations and disruptions.

By utilizing the analysis of data relative to the ranges of homeostasis and the deviations thereof, medical science (for humans as well as well as in veterinary medicine for animals) will be able to manufacture new pharmaceutical products and other substances, prepare diets, manufacture devices, create therapies, compound personalized nutrients or substances of various types in order to maintain or regulate homeostasis.

Data derived from the application of the invention will allow for diagnostic analysis and control of levels of gases in order to prevent their depletion, to maintain adequate levels to prevent disruption as well as to create recommendations for which substances may counteract with others and the levels of which substances must be modified on an ongoing basis in order to provide optimal health/well being through homeostasis.

Since nutrients, such as vitamins, minerals, electrolytes, enzymes, amino acids, proteins, etc., are essential to create defenses for the organs, glands and operating systems of the body, as well as to provide the energy to sustain life, establishing corollary relationships between gases that may require "nutrients" for their production will enable cross-category analysis to prevent depletion of the body's defense in order to prevent illness as well as to increase levels of nutritional energy to strengthen the body to offset the effects of existing ailments and diseases.

Figure 1:
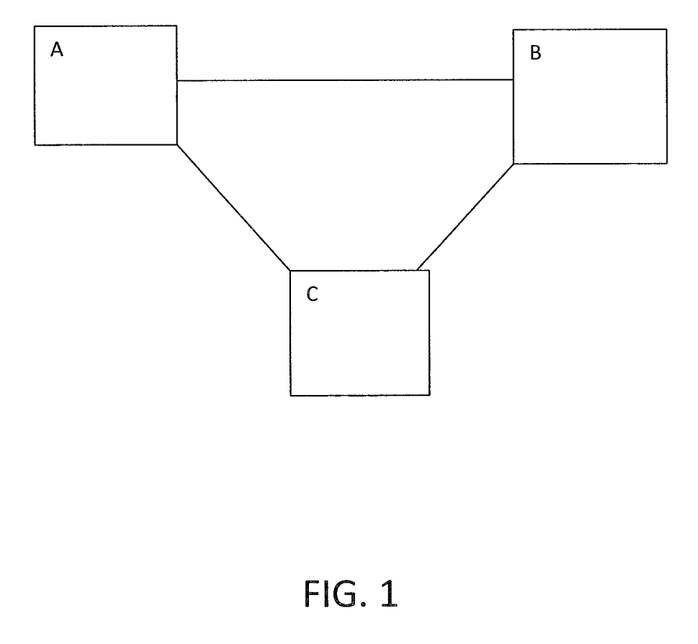
FIG. 1 illustrates the relationship of a modulated pair.

The concept of modulation in relation to homeostatic pairs is illustrated in FIG. 1. This example illustrates a relationship between two substances, A and B, and the existence of a third substance C that serves to support A or B in order to attempt to maintain an adequate level of homeostasis (balance) between the two substances.

Some examples of modulated pairs in gases within an individual include, nitric oxide and carbon dioxide modulated by hydrogen sulfide and oxygen and carbon monoxide modulated by nitric oxide.

It should be noted that some gases can function as part of a pair and also be a modulator for another pair. For example, noted above was the pair of nitric oxide and carbon monoxide, which is modulated by hydrogen sulfide. Nitric oxide also operates as a modulator for the pair of oxygen and carbon dioxide.

Correlation between base values expressed when the range of homeostasis is determined and individual test results can be used as a means of assessing levels or disruptions between pairs or the existence of increases in the levels of modulators in order to maintain homeostasis. Methods of diagnostic analysis may also detect the presence of catalysts as markers for the existence of a disruption within a modulated pair that the body is in the process of correcting. Detection of such catalysts may be included as a factor in the process of analyzing the correlation of substances within modulated pairs.

Figure 2:
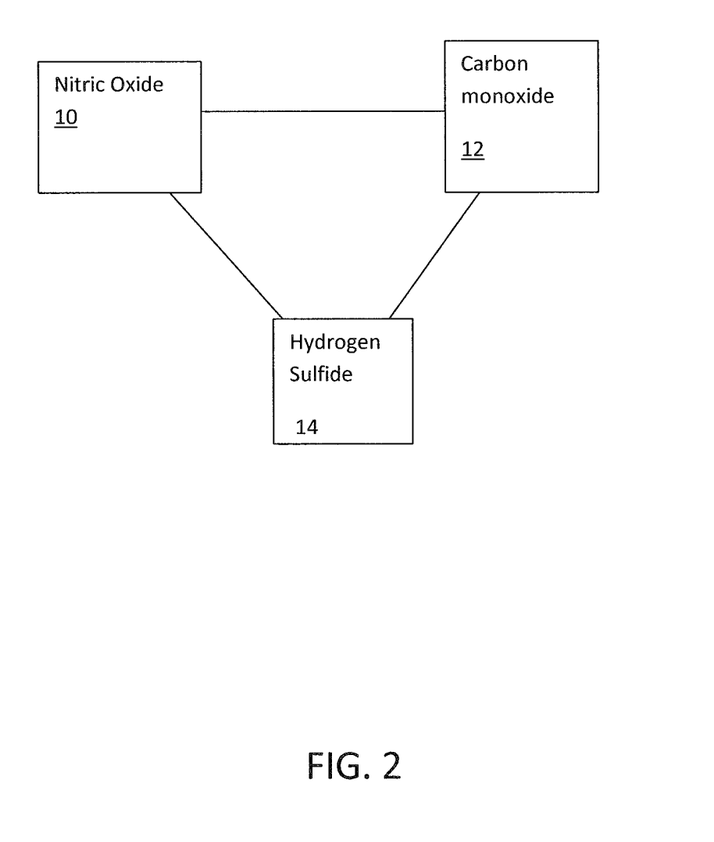
FIG. 2 shows the relationship between nitric oxide and carbon monoxide modulated by hydrogen sulfide.
Figure 3:
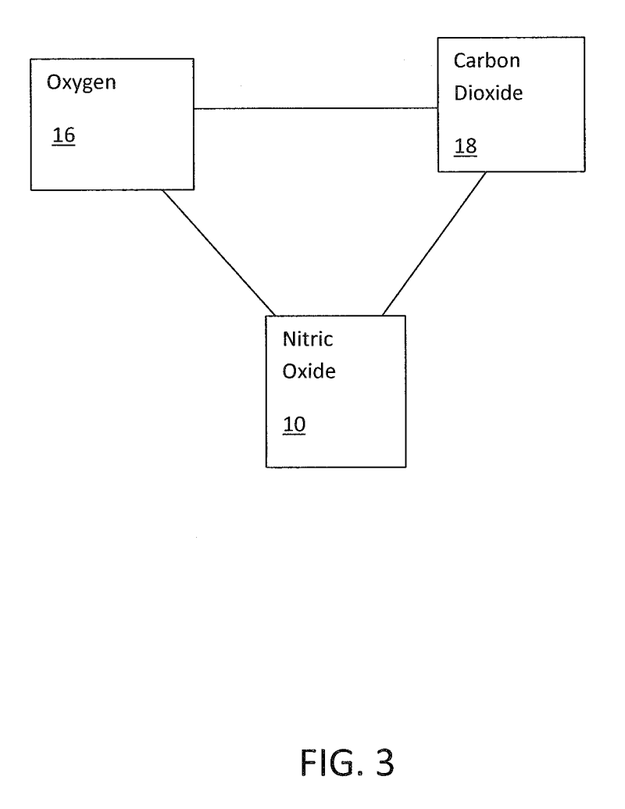
FIG. 3 shows the relationship between oxygen and carbon dioxide modulated by nitric oxide.
Figure 4:
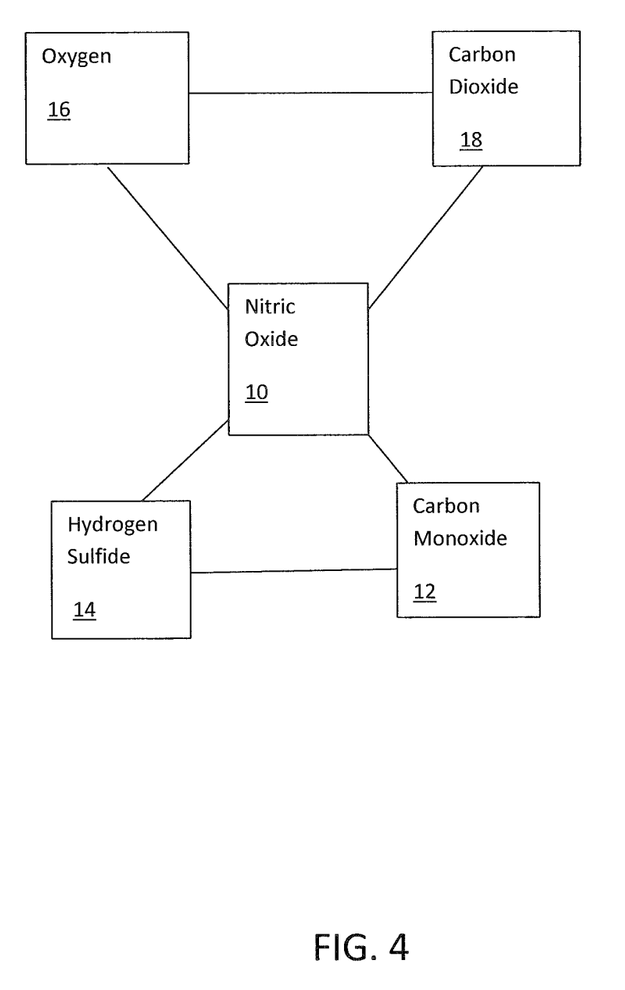
FIG. 4 shows the relationship between nitric oxide and carbon monoxide modulated by hydrogen sulfide and nitric oxide modulating oxygen and carbon dioxide.

Described herein is an example of the determination of homeostatic levels of the sets of modulated pairs discussed above. The first set is the pair of nitric oxide 10 and carbon monoxide 12 which is modulated by hydrogen sulfide 14 and the pair of oxygen 16 and carbon dioxide 18 modulated by nitric oxide 10. These relationships are shown in FIGS. 2-4. It can be seen from FIG. 4 how nitric oxide 10 is both modulated and a modulator. As such the five gases are interconnected and their interrelationship plays a role in the functioning of an individual's health processes.

Figure 5:
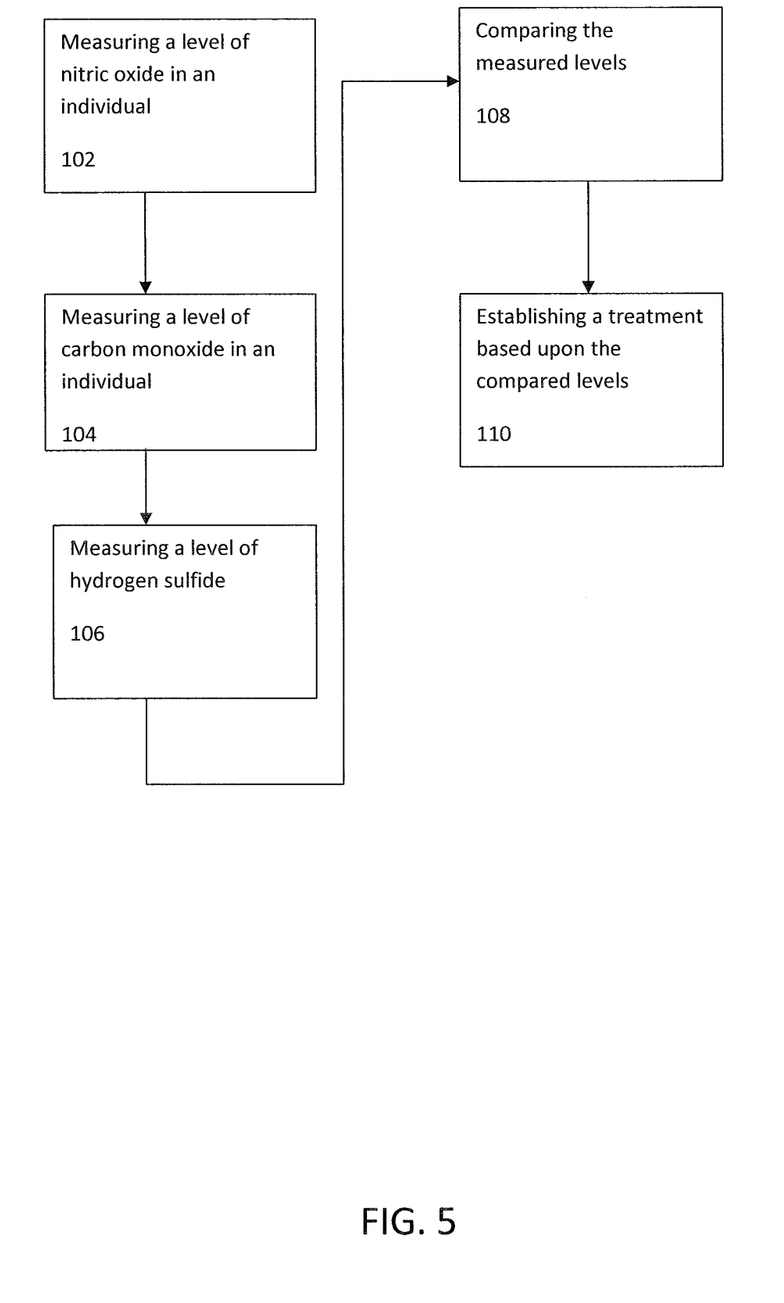
FIG. 5 shows the method of measuring levels of nitric oxide, carbon monoxide and hydrogen sulfide within an individual, in accordance with an embodiment of the present invention.

FIG. 5 shows the method of evaluating the homeostatic levels of one set of the modulated pairs in order to provide a base index for administering medication and performing analysis. In step 102 the level of nitric oxide 10 is measured in an individual. The level of nitric oxide 10 may be measured by a variety of diagnostic tests that include but are not limited to the analysis of diagnostic imaging that indicates activity and the analysis of various fluids, excretions and exhalations, within and produced by the body. Examples of these fluids and excretions include: blood and its components; serum; urine; fecal matter; collagen; chyle; interstitial fluid (tissue fluid); lymph; extracellular fluid; amniotic fluid; sweat tears; saliva; mucus; phlegm; hair; fingernails; bone marrow and exhaled breath.

In addition to the conventional diagnostic analysis of levels of substances from the aforementioned sources, various existing and yet to be developed diagnostic processes that measure outcomes resulting from these substances can be utilized. These devices may include blood gas analysis devices, devices to assess levels of gases exhaled from individuals, EEG, PET scans, use of MEG machines, SPECT analysis, functional and diffusion MRI technologies as well as other iterations thereof (fMRI and dMRI respectively), CT scans, and ultrasound. Correlation between base values expressed when the range of homeostasis is determined and individual test results may then be used as a means of assessing levels or disruptions between pairs or the existence of increases in the levels of modulators in order to maintain homeostasis. Methods of diagnostic analysis may also detect the presence of catalysts as markers for the existence of a disruption within a modulated pair that the body is in the process of remediating. Detection of such catalysts is included as a factor in the process of analyzing the correlation of substances within modulated pairs.

This invention provides the biological foundation that will enable monitoring relationships within modulated pairs of substances as they relate to medical care; including wellness, prevention and treatment pertaining to the mind (brain) and body as well as environmental issues; e.g. the quality of air and water.

The measured level of nitric oxide 10 in the body or environment may be expressed in various units depending upon the test employed in order to measure the level of the nitric oxide 10. This level can be expressed by the variable X. There is a preferred range in which X may fall that varies depending upon the type of test that is used in order to measure the level of nitric oxide 10. In an embodiment of the present invention a standard type of test is used.

In step 104 the level of carbon monoxide 12 in an individual is measured. This level can be measured using one of the various processes listed above. The measured level of carbon monoxide 12 is preferably expressed in the same units of measurement as that used in the measurement of nitric oxide 10 so as to more readily compare the levels with respect to each other in order to obtain a base level. This level can be expressed by the variable Y. There is a preferred range in which Y may fall that varies depending upon the type of test that is used in order to measure the level of carbon monoxide 12. In an embodiment of the present invention a standard type of test is used.

In step 106 the level of hydrogen sulfide 14 in an individual is measured. This level can be measured using one of the processes listed above. The measured level of hydrogen sulfide 14 is preferably expressed in the same units of measurement as that used in the measurement of nitric oxide 10 so as to more readily compare the levels with respect to each other in order to obtain a base level. This level can be expressed by the variable Z. There is a preferred range in which Z may fall that varies depending upon the type of test that is used in order to measure the level of hydrogen sulfide 14. In an embodiment of the present invention a standard type of test is used.

In step 108, the measured levels X, Y and Z are then compared to standard levels. This may be done in a number of different ways. One possible way in which this can be accomplished is to total the values of all of the levels (X+Y+Z) in order to establish sum level C. This sum level C can be used in step 110 in order to establish an appropriate treatment of the individual that may include the provision of medication and other matters related to the measured levels. Another method is to compare the ratios of X:Y, X:Z and Y:Z to determine whether or not the proper ratio levels are maintained and/or present. These ratio levels may then be used in providing an appropriate treatment.

The treatment may include, but is not limited to the provision of more hydrogen sulfide 14 to an individual. Alternatively, the reduction of hydrogen sulfide 14 may be necessitated. The provision of and/or reduction of carbon monoxide 12 and/or nitric oxide 10 may also be part of the treatment in order to return the levels of nitric oxide 10, carbon monoxide 12 and hydrogen sulfide 14 to normal levels.

An example of this is provided below using hypothetical numbers so as to make understanding of the process easier.

Measuring nitric oxide 10 via a blood test results in a number for X that results in a number 5, from within a range of 1-10. Measuring carbon monoxide 12 via a blood test results in a number for Y of 4 from within a range of 1-10. Measuring hydrogen sulfide 14 via a blood test results in a number for Z of 6 from within a range of between 1-10. These numbers are then totaled and results in a C value of 15. A value for C between 10 and 20 may indicate a normal level.

Figure 6:
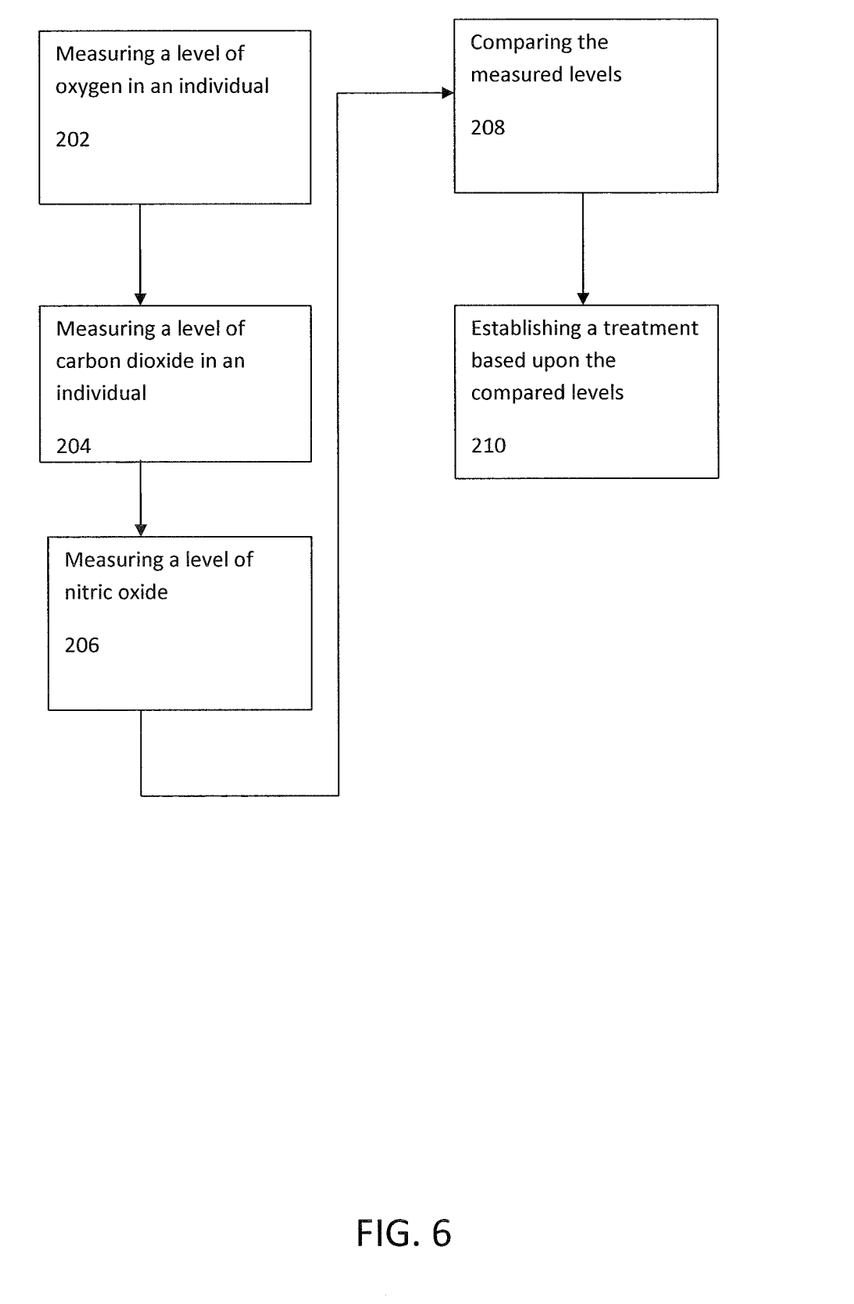
FIG. 6 shows the method of measuring levels of oxygen, carbon dioxide and nitric oxide within an individual, in accordance with an embodiment of the present invention.

The method of evaluating the homeostatic levels of the pair of oxygen 16 and carbon dioxide 18 modulated by nitric oxide 10 may be used in order to provide a base index for administering medication and to perform behavioral analysis. This method is shown in FIG. 6. In step 202 the level of oxygen 16 is measured in an individual. The level of oxygen 16 may be measured by a variety of diagnostic tests similar to that discussed above that include but are not limited to the analysis of diagnostic imaging that indicates activity and the analysis of various fluids and excretions within and produced by the body. Examples of these fluids and excretions include: blood and its components, serum; urine; fecal matter; collagen; chyle; interstitial fluid (tissue fluid); lymph; extracellular fluid; amniotic fluid; sweat tears; saliva; mucus; phlegm; hair; fingernails; bone marrow. The measured level of oxygen 16 in the body is expressed in various units depending upon the test employed in order to measure the level of the oxygen 16. This level can be expressed by the variable X. There is a preferred range in which X may fall that varies depending upon the type of test that is used in order to measure the level of oxygen 16. In an embodiment of the present invention a standard type of test is used.

In step 204 the level of carbon dioxide 18 in an individual is measured. This level can be measured using one of the various processes listed above. The measured level of carbon dioxide 18 is preferably expressed in the same units of measurement as that used in the measurement of oxygen 16 so as to more readily compare the levels with respect to each other in order to obtain a base level. This level can be expressed by the variable Y. There is a preferred range in which Y may fall that varies depending upon the type of test that is used in order to measure the level of carbon dioxide 18. In an embodiment of the present invention a standard type of test is used.

In step 206 the level of nitric oxide 10 in an individual is measured. This level can be measured using one of the various processes listed above. The measured level of nitric oxide 10 is preferably expressed in the same units of measurement as that used in the measurement of oxygen 16 so as to more readily compare the levels with respect to each other in order to obtain a base level. This level can be expressed by the variable Z. There is a preferred range in which Z may fall that varies depending upon the type of test that is used in order to measure the level of nitric oxide 10. In an embodiment of the present invention a standard type of test is used.

In step 208, the measured levels X, Y and Z are then compared to standard levels. This may be done in a number of different ways. One possible way in which this can be accomplished is to total the values of all of the levels (X+Y+Z) in order to establish sum level C. This sum level C can be used in step 210 in order to establish a treatment of the individual that can be used in determining the provision of medication and other matters related to the measured levels.

The treatment may include, but is not limited to the provision of more nitric oxide 10 to an individual. Alternatively, the reduction of nitric oxide 10 may be necessitated. The provision of and/or reduction of carbon dioxide 18 and/or oxygen 16 may also be part of the treatment in order to return the levels of nitric oxide 10, oxygen 16 and carbon dioxide 18 to normal levels.

An example of this is provided below using hypothetical numbers to make understanding of the process easier.

Measuring oxygen 16 via a blood test results in a number for X that results in a number 4, from within a range of 1-10. Measuring carbon monoxide 18 via a blood test results in a number for Y of 5 from within a range of 1-10. Measuring nitric oxide 10 via a blood test results in a number for Z of 7 from within a range of between 1-10. These numbers are then totaled and results in a C value of 16. A value for C between 12 and 18 may indicate a normal level.

The assessment of the modulated pairs of gases enables the provision of consulting/counseling services relative to the biological foundation for and between the gases and neurohormones associated with logic/decision making and emotions for the purpose of enhancing or remediating intellect or behavioral outcomes for children, students, employees and patients.

The assessment of the modulated pairs of gases may be used to provide training counselors or other personnel associated with the care or treatment of individuals who are experiencing disruptions in thought processes (including but not limited to Asperger's, ADHD, ADD, dementia, forms of over focus, etc.) as well as emotional disruptions (including but not limited to Obsessive-Compulsive Disorder (OCD), Oppositional Defiant Disorder (ODD), Post Traumatic Stress Disorder (PTSD), and depression). These training methods will include the use of graphic illustrations; computer generated information, printed and video material, as well as verbal instructional information pertaining to the homeostasis or relationship of or between neurohormones in pairs as well as in modulated pairs.

The assessment of the modulated pairs of gases may also be used for creating a baseline assessment of an individual's homeostatic levels of activity within modulated pairs of gases for the purpose of establishing a foundation from which prevention of illnesses, treatment regimens or educational planning can be optimized.

The assessment of the modulated pairs of gases may also be used for the manufacture, sale, or use of devices for the purpose of reconfiguring gases or adjusting levels for the purpose of modifying behavior or improving mental health as well as for use in Neurohormone Reconfiguration$^{SM}$ or as part of neuroplasticity when treating patients with cognitive or emotional disorders due to injury or illness.

The assessment of the modulated pairs of gases may also be used for the manufacture, sale or use of devices to monitor MFA or to be used in conjunction with processes intended to perform Reflective Meditation$^{SM}$.

The assessment of the modulated pairs of gases may also be used for the manufacture, sale or use of devices to measure MFA as a means of assessing intellectual capabilities, such as IQ.

The assessment of the modulated pairs of gases may also be used for the manufacture, sale or use of devices to assess biometric indicators to determine absorption rate of cells as a means of assessing susceptibility for illnesses or sensitivity to foods, herbs, medications or environmental irritants and potential toxins.

The assessment of the modulated pairs of gases may also be used for the manufacture, sale or use of devices to create or assess biometric indicators to determine possible causes of lupus, cancer and other chronic diseases and also be used as a tool to assist with processes to reduce MFA as part of treatment regimens.

The assessment of the modulated pairs of gases may also be used for enabling diagnostic assessment of values of gases in relation to others within a modulated pair or between modulated pairs.

The assessment of the modulated pairs of gases may also be used for assessing the impact of various substances on the modulated pairs responsible for the firing rate of neurons and signaling mechanisms and their impact on the body's rates of activities will enable scientists and medical professionals to diagnose root causes of diseases and disorders. This aspect of the invention can enable evaluation of the impact of disruptions from imbalances in amino acid neurotransmitters or cellular adhesion that may cause hormone, organ or gland imbalances. Assessment of these processes can prevent diseases or enable treatment regimens for diabetes, obesity resulting from disruptions for when to store fat, thyroid imbalances as well as numerous other disease entities.

The assessment of the modulated pairs of gases may also be used for the assessment (diagnostic testing) of the impact on the relationship of gases within modulated pairs by any substances ingested or absorbed by the body relative to neural firing rates (i.e. aspartate—gamma aminobutyric acid—glutamate).

The assessment of the modulated pairs of gases may also be used for the assessment of neurohormone levels to gauge intellectual capacity or capabilities (e.g. IQ).

The assessment of the modulated pairs of gases may also be used as a tool for assessment of or modification to thought patterns or behavior in business applications by trained specialists in categorization of behavioral characteristics, consultants, management personnel including executives or educational personnel associated with employee training or organizational development processes. These processes can be for individuals, groups such as teams or work units as well as entire corporations or portions thereof.

The assessment of the modulated pairs of gases may also be used for the application of the tenets of neurobiology (i.e. Neurohormone Reconfiguration$^{SM}$, modification to neural architecture through neural plasticity or alteration of neural firing rates) as the concept applies to the modification or creation of cultures in business (including but not limited to healthcare), academia or scientific research.

The assessment of the modulated pairs of gases may also be used for publishing of information and provision of consulting, counseling or educational services relative to the biological foundation for and between the gases associated with logic/decision making and emotions for the purpose of enhancing or remediating intellect for behavioral outcomes for children, students, employees and patients.

The assessment of the modulated pairs of gases may also be used in counseling, coaching, consulting and other services provided as part of personalized (precision—explicit) medicine or other services provided as part of spa treatments or related activities associated with wellness or preventative, or therapeutic treatments.

The assessment of the modulated pairs of gases may also be used for forms of testing or assessment of gas levels or disruptions to modulated pairs to ascertain the existence of Hormone Induced Detachment$^{SM}$ ("burnout"), Asperger's, ADHD, ADD, dementia, forms of over focus, etc.) as well as emotional disruptions (including but not limited to Obsessive-Compulsive Disorder (OCD), Oppositional Defiant Disorder (ODD), Post Traumatic Stress Disorder (PTSD), and depression).

The assessment of the modulated pairs of gases may also be used for clinical and other counseling and treatment programs as well as communities of practice (e.g. Weight Watchers, Alcoholics Anonymous, and services for Obsessive-Compulsive Disorders and addictions; including but not limited to smoke cessation, dieting, and substance abuse that incorporate education and training relative to modulated pairs of gases, assessment of neural firing rates (i.e. mental functioning activity—MFA) and the ability to reconfigure the wiring in the brain through the process of Neurohormone Reconfiguration$^{SM}$ or the process of Reflective Meditation$^{SM}$.

The usage of these methods can also be used with devices that will measure levels of the gases contained within the body that include those listed in the invention and assess the corollary relationships between these gases in order to compare them to standard biodiagnostic baseline assessment.

The usage of these methods can also be used with devices that measure the levels of the gases listed in the invention that are in the environment, such as the air, and assess the corollary relationships between these gases in order to compare them to standards established for proper air quality.

The usage of these methods can also be used with devices that measure the levels of the gases listed in the invention that are in water, inland as well as seas and oceans and stored for use in air conditioning and drinking purposes, and assess the corollary relationships between these gases in order to compare them to standards established for proper water quality.

The usage of these methods can also be used for medications (prescription and over the counter) and herbal preparations that can be prepared to correct imbalances between normal values that are established for the substances that comprise the modulated pairs of substances listed in this invention.

The usage of these methods can also be used for assessment of homeostatic imbalances of relationships within modulated pairs that can enable therapies to correct these disruptions instead of waiting to the point where mental or physical consequences will require expensive or sophisticated treatment of ailments or diseases that are the outcomes.

The usage of these methods can also be used to ascertain disruptions of the base values of the relationships within the modulated pairs of the substances listed in this invention that can have various negative impacts throughout the body and the brain. Diseases and disorders that can be directly attributable to multiple concurrent disruptions of homeostasis established with modulated pairs can include but are not be limited to various types of cancers, Parkinson's, Asperger's, Alzheimer's, end stage renal disease, obstructive sleep apnea, insomnia, diabetes, obesity as well as the diseases associated with the formation of and processes associated with connective tissue and smooth muscle that comprises veins, arteries, organs and glands, etc.

Assessment of the impact of various substances on the modulated pairs responsible for the firing rate of neurons and signaling mechanisms and their impact on the body's rates of activities enable scientists and medical professionals to diagnose root causes of diseases and disorders. This aspect of the invention can enable evaluation of the impact of disruptions from imbalances in gasotransmitters (gases that are contained within the body that function as components of signaling molecules) that maintain mechanisms that may cause DNA, RNA, nucleotide, hormone, organ or gland imbalances. Assessment of these processes can prevent diseases or enable treatment regimens for cardiovascular diseases, obstructive sleep apnea, prevention or treatment of parasitic diseases, and the degree of flexibility of the body's skin, veins, arteries and organs as well as numerous other disease entities.

The usage of these methods can also be used for the design of devices to correlate the relationship between the various gases contained in the body as listed in this invention. These devices can include but should not be limited to ones used within the veins and arteries, ongoing assessment as implanted devices, monitoring devices for home use or those used to perform diagnostic assessments in physicians offices, hospitals, diagnostic laboratories, home care or any other setting where the analysis of these gases contained in the blood are measured and compared to each other to perform assessments to maintain proper health and well being. A schematic of the system diagram is shown in FIG. 7.

Figure 7:
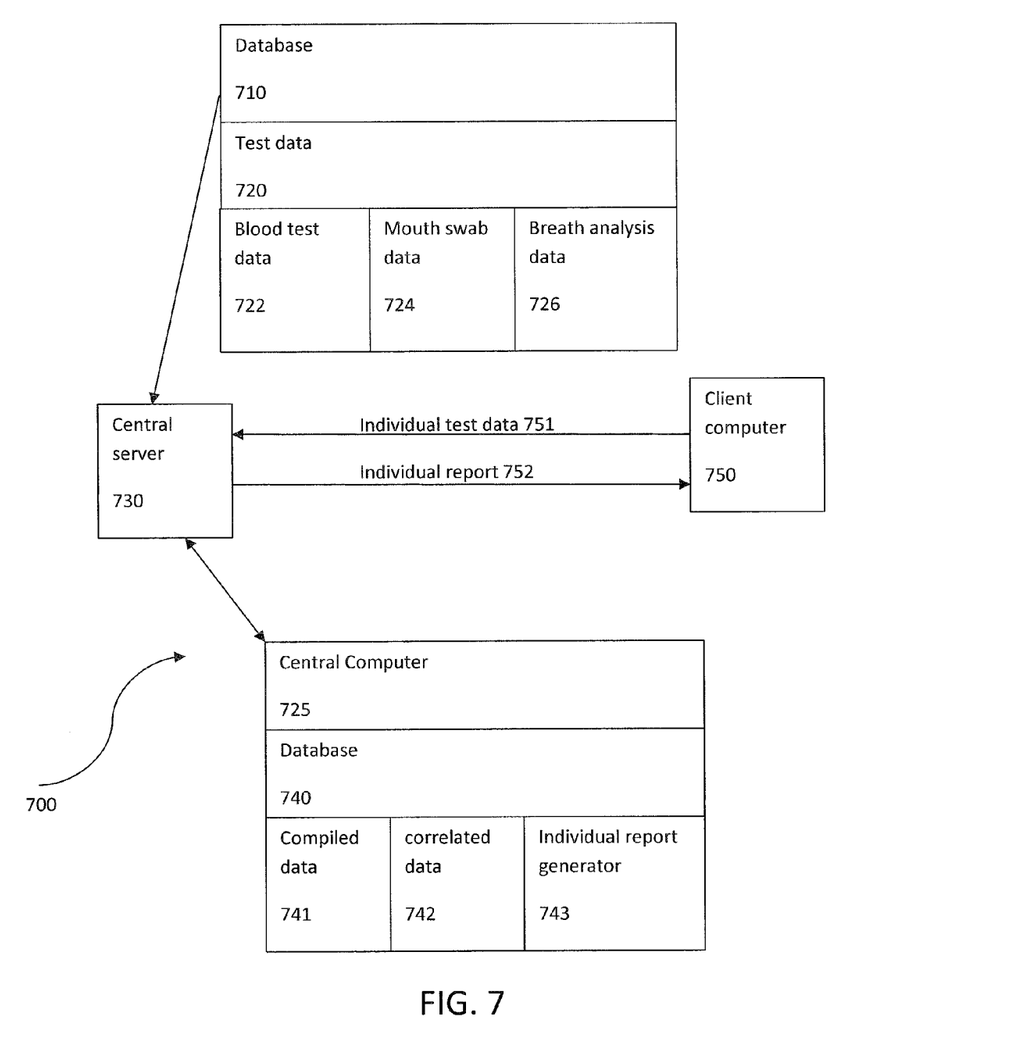
FIG. 7 is a schematic diagram showing the system for measuring the levels of gases contained within the body.
Figure 8:
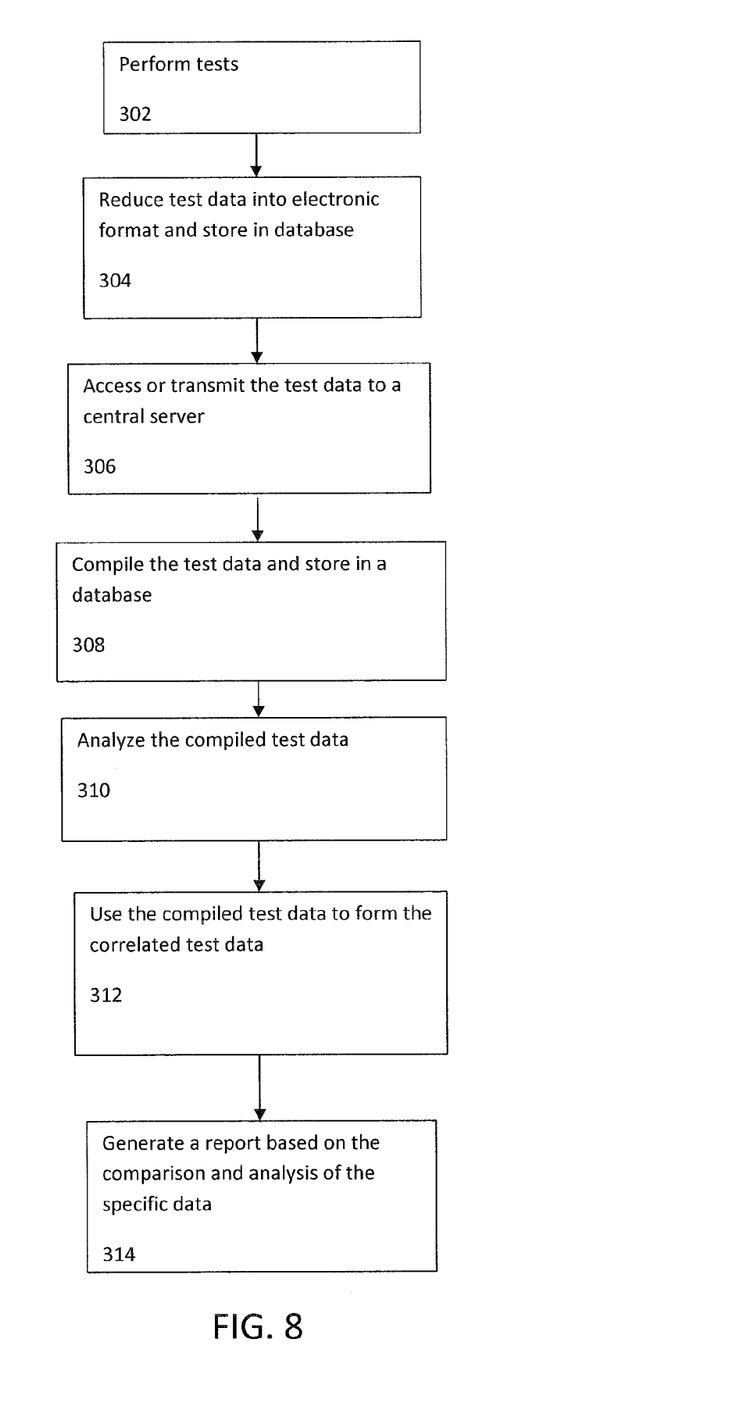
FIG. 8 is a flow chart showing the steps involved in using the system shown in FIG. 7.

FIG. 7 shows a personalized report generator system 700 designed and arranged in accordance with an embodiment of the present invention. It should be understood that the system 700 shows the basic components of the system and that more or less individualized components may be provided. FIG. 8 is a flow chart showing the steps involved in using the system 700.

The personalized report generator system 700 comprises a database 710 in which may be stored various test results, which are stored in the database 710 as test data 720. The test data 720 is in a format that is capable of being manipulated by computers, processors, etc. The test data 720 may comprise various gas levels. In an exemplary embodiment of the present invention and shown in step 302, tests are performed on individual patients. In step 304, the results of these tests are then reduced into an electronic format in order to produce the test data 720. For example, the database 710 may store blood test data 722, mouth swab data 724 and breath analysis data 726. Other tests may include urine; fecal matter; collagen; chyle; interstitial fluid (tissue fluid); lymph; extracellular fluid; amniotic fluid; sweat tears; saliva; mucus; phlegm; hair; fingernails; and bone marrow. Each of these various tests may screen for a plurality of gases. As an example, the breath analysis data 726 may screen for nitric oxide, carbon dioxide or hydrogen sulfide. Performing a breath analysis may done using testing kits that test for a specific gas, such as nitric oxide, or done via analysis in a lab setting. More than one kit may used for each gas tested for.

The test data 720 may be organized and stored at the database 710. Alternatively, satellite locations may each maintain their own databases 710 that control their own records. In step 306, these locations may be accessed periodically by the central server 730 or the various databases 710 may transmit their results to a central location that is then accessible by a central server 730. Preferably the test data 720 is only accessed or transmitted when a certain threshold number of results are obtained. For example the test data 720 may not be sent to the central server 730 until at least one hundred tests are prepared to be transmitted.

In step 308, the transmitted test data 720 is compiled and stored as compiled test data 741. The central server 730 may keep the sent or accessed compiled test data 741 stored at its location in the central database 740, or the system 700 may provide a distributed storage system that stores the compiled test data 741 at external locations as well as the central database 740. However it should be understood that when compiled test data 741 is stored at distributed sites the system still functions as if they were stored at the central database 740. The compiled test data 741 may be stored so that the origin of the data is maintained in an anonymous fashion. In some instances tracking of the origin of a test result may only occur when a personalized report is requested.

In step 310, the compiled test data 741 is then analyzed in order to determine significant figures for conducting analysis. The analysis may be accomplished with the usage of a computer(s) 725 of which the server 730 may be a part of, as well as the database 710. The analysis may be accomplished by statistically compiling and correlating the results for one specific test or by compiling the data for two separate items that are believed to have a relationship. Specific values from the plurality of compiled test data 741 having a similar feature may be analyzed. This may be accomplished through the application of known statistical algorithms. In step 312, the statistically compiled test data 741 may be used to form the correlated data 742. In step 314, the statistically correlated data 742 are then used by the individual report generator 743 to form the personalized medical prescription and diagnosis. Upon receipt of individual test data 751 from a client computer 750, the individual report generator 743 processes the data and transmits an individual report 752 to a client computer 750.

The compiled test data 741 may be periodically updated from the databases 710 and through the addition of more collected test data. The updating of the compiled test data 741 may provide additional information with which to refine the correlated data 742 and to refine the ranges used by the individual report generator 743 when producing the personalized medical prescription and diagnosis. Additionally the updating of the compiled test data 741 may be a continuous feature wherein the addition of new information is immediately reflected in the correlated data 742. This may provide for a constantly fluid analysis of compiled test data 741 that may reflect changes in population and diets in society.

The usage of these methods can also be used for the design of devices to correlate the relationship between the various gases contained in the environment (air) as listed in this invention. These devices can include but should not be limited to ones used within homes, public transportation, the work-place (buildings), stores and other commercial building or places where people gather as well as for general monitoring of air quality as established in the future. A schematic of the system diagram is shown in FIG. 9.

Figure 9:
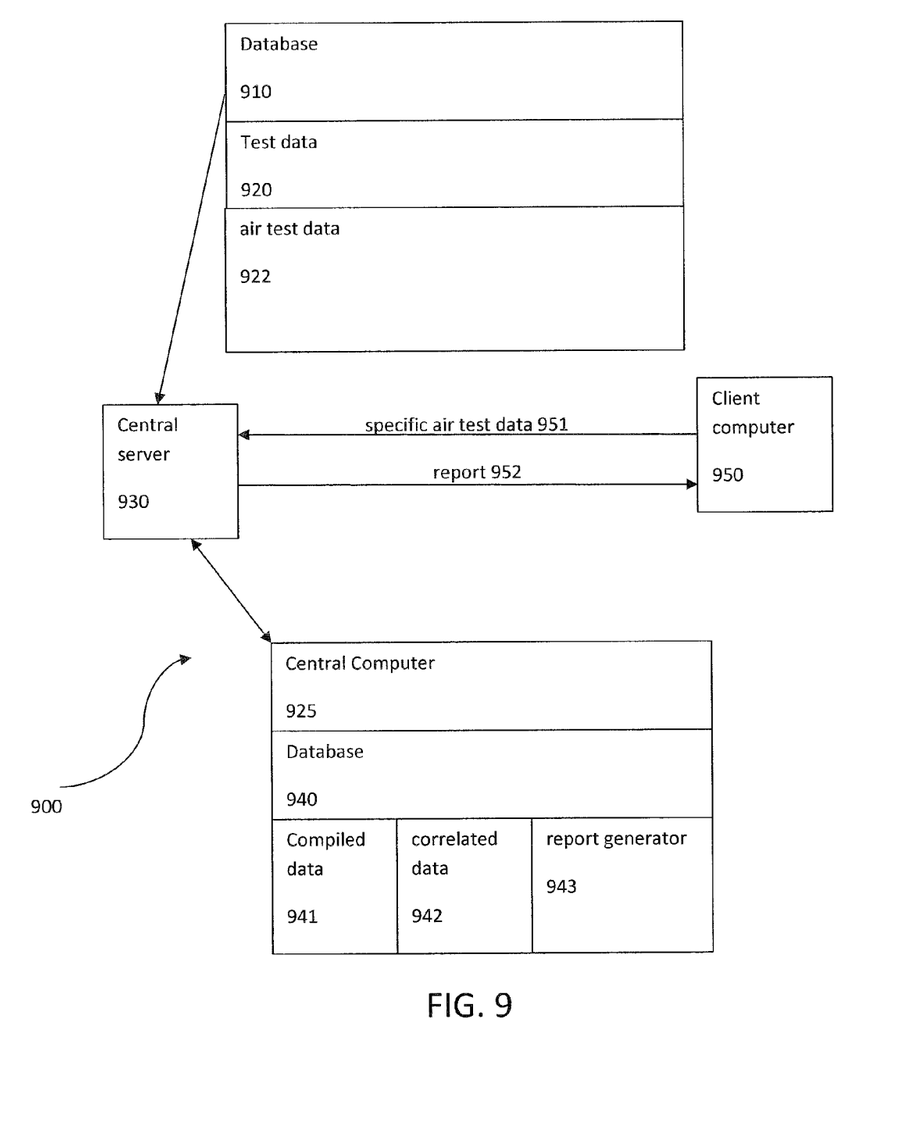
FIG. 9 is a schematic diagram showing the system for measuring the levels of gases contained within the atmosphere or environment.
Figure 10:
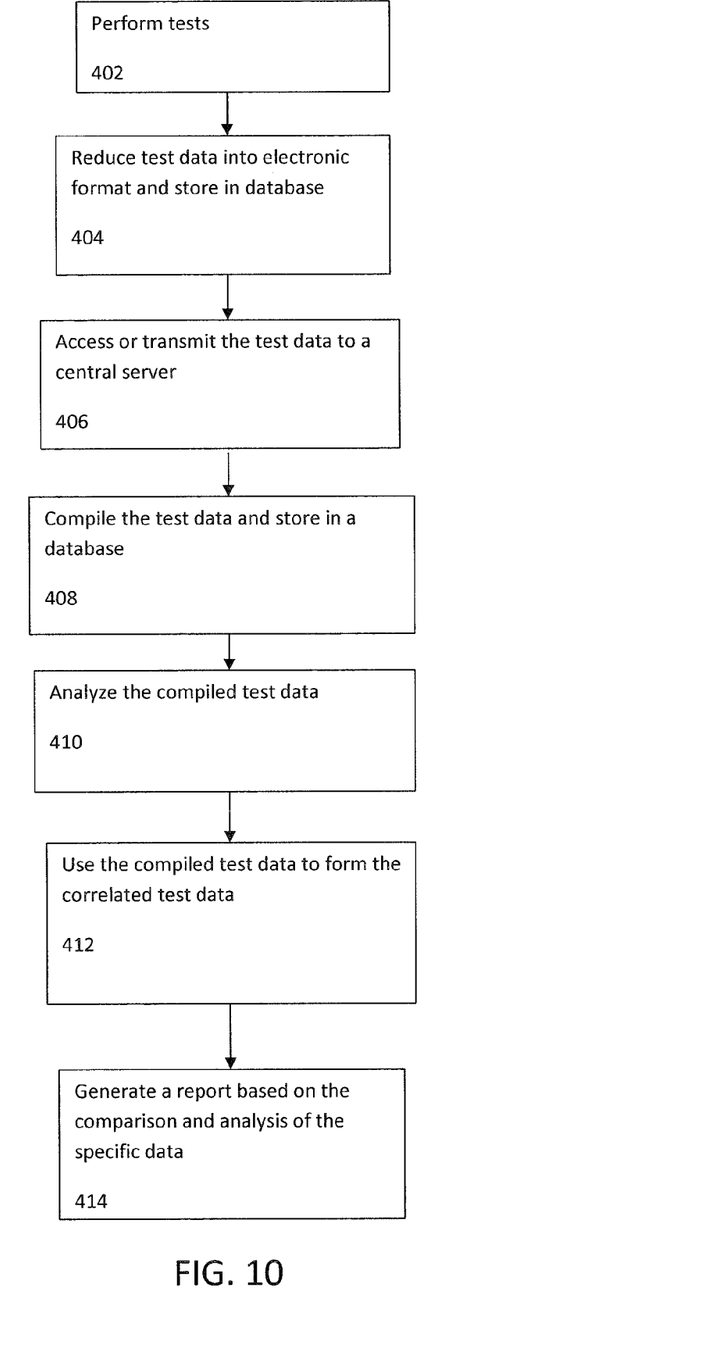
FIG. 10 is a flow chart showing the steps involved in using the system shown in FIG. 9.

FIG. 9 shows a report generator system 900 designed and arranged in accordance with an embodiment of the present invention. It should be understood that the system 900 shows the basic components of the system and that more or less individualized components may be provided. FIG. 10 is a flow chart showing the steps involved in using the system 900.

The report generator system 900 comprises a database 910 in which may be stored various test results, which are stored in the database 910 as test data 920. The test data 920 is in a format that is capable of being manipulated by computers, processors, etc. The test data 920 may comprise various gas levels. In an exemplary embodiment of the present invention and shown in step 402, tests are performed on gaseous environments, such as the atmosphere, a room's environment, etc. In step 404, the results of these tests are then reduced into an electronic format in order to produce the test data 920. For example, the database 910 may store air test data 922.

Each of these tests may screen for a plurality of physical compound levels of different gases. As an example, air test data 922 may screen for oxygen, nitric oxide, carbon dioxide, carbon monoxide or hydrogen sulfide. Testing may be performed using standard testing devices and analysis kits. For example, mass spectrometry of samples taken from water to be tested may be tested using kits such as that described in U.S. Pat. No. 5,101,671. Air samples may be collected on site and sent to a lab for analysis. Alternatively, samples may be collected and tests for targeted gases may be performed on site.

The test data 920 may be organized and stored at the database 910. Alternatively, satellite locations may each maintain their own databases 910 that control their own records. In step 406, these locations may be accessed periodically by the central server 930 or the various databases 910 may transmit their results to a central location that is then accessible by a central server 930. Preferably the test data 920 is only accessed or transmitted when a certain threshold number of results are obtained. For example the test data 920 may not be sent to the central server 930 until at least one hundred tests are prepared to be transmitted.

In step 408, the transmitted test data 920 is compiled and stored as compiled test data 941. The central server 930 may keep the sent or accessed compiled test data 941 stored at its location in the central database 940, or the system 900 may provide a distributed storage system that stores the compiled test data 941 at external locations as well as the central database 940. However, it should be understood that when compiled test data 941 is stored at distributed sites the system still functions as if they were stored at the central database 940. The compiled test data 941 may be stored so that the origin of the data is maintained in an anonymous fashion. In some instances tracking of the origin of a test result may only occur when a personalized report is requested.

In step 410, the compiled test data 941 is then analyzed in order to determine significant figures for conducting analysis. The analysis may be accomplished with the usage of a computer(s) 925 of which the server 930 may be a part of, as well as the database 910. The analysis may be accomplished by statistically compiling and correlating the results for one specific test or by compiling the data for two separate items that are believed to have a relationship. Specific values from the plurality of compiled test data 941 having a similar feature may be analyzed. This may be accomplished through the application of known statistical algorithms. In step 412, the statistically compiled test data 941 may be used to form the correlated data 942. In step 414, the statistically correlated data 942 is then used by the report generator 943 to form the personalized medical prescription and diagnosis. Upon receipt of individual test data 951 from a client computer 950, the report generator 943 processes the data and transmits an individual report 952 to a client computer 950.

The compiled test data 941 may be periodically updated from the databases 910 and through the addition of more collected test data. The updating of the compiled test data 941 may provide additional information with which to refine the correlated data 942 and to refine the ranges used by the report generator 943 when producing the results of the analysis. Additionally the updating of the compiled test data 941 may be a continuous feature wherein the addition of new information is immediately reflected in the correlated data 942. This may provide for a constantly fluid analysis of compiled test data 941 that may reflect changes in the environment.

Treatment may involve the employment of devices for scrubbing various gases from the atmosphere of a given environment. For example, if the environment was a particular room or building, filters or air purifiers designed to filter out specific gases may be employed in order to return a select environment to homeostatic balance. This may also involve adding select gases to the environment instead of reducing levels of a select gas.

The usage of these methods can also be used for the design of devices to correlate the relationship between various gases contained in water. The location of this water includes but is not limited to inland streams, rivers, ponds and lakes; seas and oceans as well as in water treatment towers associated with air conditioning and water storage for consumption by humans and animals and assess the corollary relationships between these gases in order to compare them to standards establish for proper water quality. A schematic of the system diagram is shown in FIG. 11.

Figure 11:
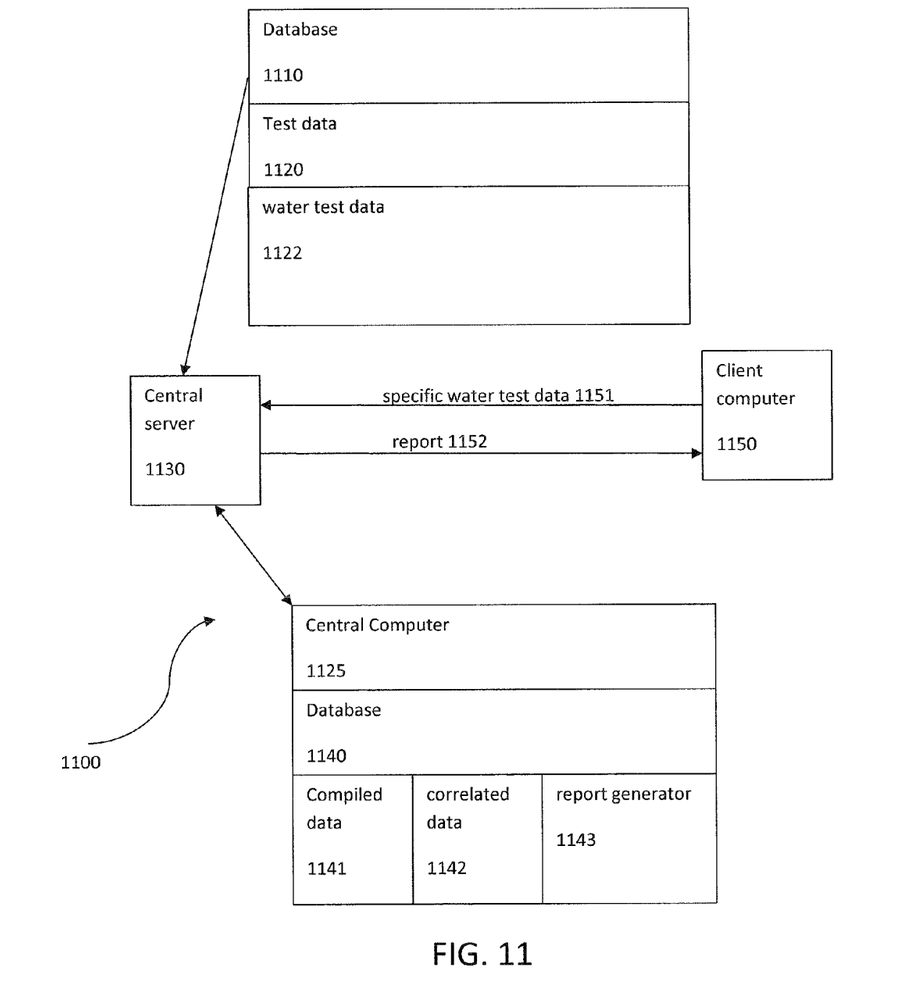
FIG. 11 is a schematic diagram showing the system measuring the levels of gases within water.
Figure 12:
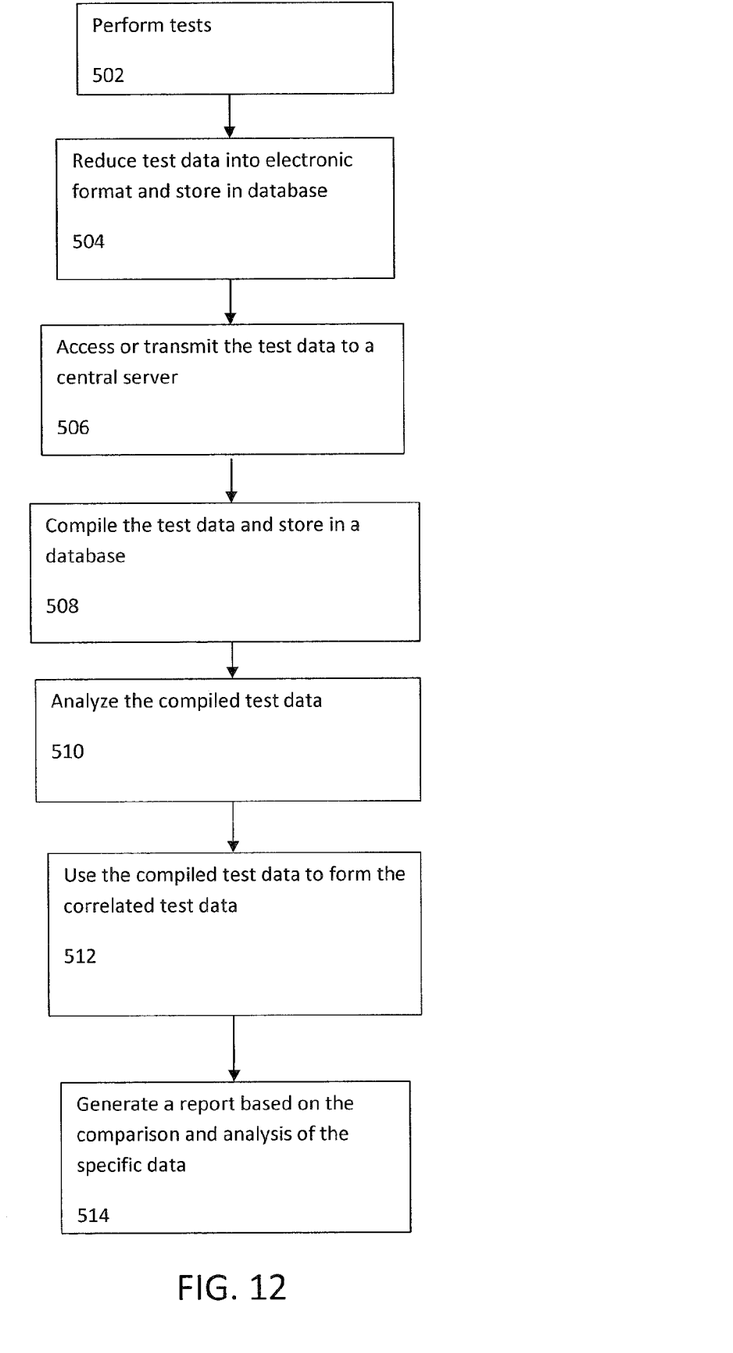
FIG. 12 is a flow chart showing the steps involved in using the system shown in FIG. 11.

FIG. 11 shows a report generator system 1100 designed and arranged in accordance with an embodiment of the present invention. It should be understood that the system 1100 shows the basic components of the system and that more or less individualized components may be provided. FIG. 12 is a flow chart showing the steps involved in using the system 1100.

The report generator system 1100 comprises a database 1110 in which may be stored various test results, which are stored in the database 1110 as test data 1120. The test data 1120 is in a format that is capable of being manipulated by computers, processors, etc. The test data 1120 may comprise various gas levels. In an exemplary embodiment of the present invention and shown in step 502, tests are performed on gaseous environments, such as the atmosphere, a room's environment, etc. In step 504, the results of these tests are then reduced into an electronic format in order to produce the test data 1120. For example, the database 1110 may store water test data 1122.

Each of these tests may screen for a plurality of physical compound levels of different gases. As an example, water test data 1122 may screen for oxygen, nitric oxide, carbon dioxide, carbon monoxide or hydrogen sulfide. Testing may be performed using standard water testing devices and analysis kits. For example, mass spectrometry of samples taken from water to be tested may be used.

The test data 1120 may be organized and stored at the database 1110. Alternatively, satellite locations may each maintain their own databases 1110 that control their own records. In step 506, these locations may be accessed periodically by the central server 1130 or the various databases 1110 may transmit their results to a central location that is then accessible by a central server 1130. Preferably the test data 1120 is only accessed or transmitted when a certain threshold number of results are obtained. For example the test data 1120 may not be sent to the central server 1130 until at least one hundred tests are prepared to be transmitted.

In step 508, the transmitted test data 1120 is compiled and stored as compiled test data 1141. The central server 1130 may keep the sent or accessed compiled test data 1141 stored at its location in the central database 1140, or the system 1100 may provide a distributed storage system that stores the compiled test data 1141 at external locations as well as the central database 1140. However, it should be understood that when compiled test data 1141 is stored at distributed sites the system still functions as if they were stored at the central database 1140. The compiled test data 1141 may be stored so that the origin of the data is maintained in an anonymous fashion. In some instances tracking of the origin of a test result may only occur when a personalized report is requested.

In step 510, the compiled test data 1141 is then analyzed in order to determine significant figures for conducting analysis. The analysis may be accomplished with the usage of a computer(s) 1125 of which the server 1130 may be a part of, as well as the database 1110. The analysis may be accomplished by statistically compiling and correlating the results for one specific test or by compiling the data for two separate items that are believed to have a relationship. Specific values from the plurality of compiled test data 1141 having a similar feature may be analyzed. This may be accomplished through the application of known statistical algorithms. In step 512, the statistically compiled test data 1141 may be used to form the correlated data 1142. In step 514, the statistically correlated data 1142 is then used by the report generator 1143 to form the personalized medical prescription and diagnosis. Upon receipt of individual test data 1151 from a client computer 1150, the report generator 1143 processes the data and transmits an individual report 1152 to a client computer 1150.

The compiled test data 1141 may be periodically updated from the databases 1110 and through the addition of more collected test data. The updating of the compiled test data 1141 may provide additional information with which to refine the correlated data 1142 and to refine the ranges used by the report generator 1143 when producing the results of the analysis. Additionally the updating of the compiled test data 1141 may be a continuous feature wherein the addition of new information is immediately reflected in the correlated data 1142. This may provide for a constantly fluid analysis of compiled test data 1141 that may reflect changes water content.

Treatment may involve the employment of devices for scrubbing various gases from the water. For example, if the environment was a stream, filters may be employed to filter out specific gases in order to return the water to homeostatic balance. This may also involve adding select gases to the water instead of reducing levels of a select gas.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method for establishing a treatment by comparing levels of gases in water comprising: measuring a level of nitric oxide in the water; measuring a level of carbon monoxide in the water; measuring a level of hydrogen sulfide in the water; comparing the measured levels of nitric oxide, carbon monoxide and hydrogen sulfide to standard levels in water; and establishing a treatment based upon the compared measured levels.

2. The method of claim 1, comprising measuring a level of oxygen in the water; measuring a level of carbon dioxide in the water; comparing the measured or assessed levels; and providing treatments based upon the compared measured levels.

3. The method of claim 1, wherein the level of carbon monoxide is measured by a device for testing the water.

4. The method of claim 3, further comprising measuring a level of oxygen in the water; and measuring a level of carbon dioxide in the water.

5. The method of claim 1, wherein the treatment comprises reducing nitric oxide in the water.

6. The method of claim 1, wherein the treatment comprises reducing carbon monoxide in the water.

\* \* \* \* \*